United States Patent
Ryterski et al.

(10) Patent No.: US 9,168,102 B2
(45) Date of Patent: Oct. 27, 2015

(54) METHOD AND APPARATUS FOR PROVIDING A CONTAINER TO A STERILE ENVIRONMENT

(75) Inventors: Eric Ryterski, Louisville, CO (US); Lance Kendrick, Lafayette, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 2587 days.

(21) Appl. No.: 11/334,798

(22) Filed: Jan. 18, 2006

(65) Prior Publication Data
US 2007/0166188 A1 Jul. 19, 2007

(51) Int. Cl.
*A61B 19/00* (2006.01)
*A61B 19/08* (2006.01)
*A61B 19/02* (2006.01)

(52) U.S. Cl.
CPC ....... *A61B 19/081* (2013.01); *A61B 2019/0267* (2013.01); *A61B 2019/0286* (2013.01)

(58) Field of Classification Search
USPC .................................. 606/1; 128/849; 422/1
See application file for complete search history.

(56) References Cited

U.S. PATENT DOCUMENTS

| | | | |
|---|---|---|---|
| 1,576,781 A | 3/1926 | Phillips | |
| 1,735,726 A | 11/1929 | Bornhardt | |
| 2,246,596 A | 6/1941 | Moore | |
| 2,407,845 A | 9/1946 | Nemeyer | |
| 2,537,303 A | 1/1951 | Cobb, Jr. et al. | |
| 2,650,588 A | 9/1953 | Drew | |
| 2,697,433 A | 12/1954 | Sehnder | |
| 3,016,899 A | 1/1962 | Stenvall | |
| 3,017,887 A | 1/1962 | Heyer | |
| 3,061,936 A | 11/1962 | Dobbeleer | |
| 3,073,310 A | 1/1963 | Mocarski | |
| 3,109,588 A | 11/1963 | Polhemus et al. | |
| 3,294,083 A | 12/1966 | Alderson | |
| 3,315,877 A | 4/1967 | Grevich | |
| 3,367,326 A | 2/1968 | Frazier | |
| 3,439,256 A | 4/1969 | Kähne et al. | |
| 3,577,160 A | 5/1971 | White | |
| 3,614,950 A | 10/1971 | Rabey | |
| 3,644,825 A | 2/1972 | Davis, Jr. et al. | |
| 3,674,014 A | 7/1972 | Tillander | |
| 3,702,935 A | 11/1972 | Carey et al. | |
| 3,704,707 A | 12/1972 | Halloran | |
| 3,746,215 A | 7/1973 | Ausnit et al. | |
| 3,821,469 A | 6/1974 | Whetstone et al. | |
| 3,865,304 A * | 2/1975 | Mojonnier et al. | 383/82 |
| 3,868,565 A | 2/1975 | Kuipers | |

(Continued)

FOREIGN PATENT DOCUMENTS

| | | |
|---|---|---|
| CA | 964149 | 3/1975 |
| DE | 3036217 | 4/1982 |

(Continued)

OTHER PUBLICATIONS

Adams et al., Computer-Assisted Surgery, IEEE Computer Graphics & Applications, pp. 43-51, (May 1990).

(Continued)

*Primary Examiner* — William Thomson
*Assistant Examiner* — Jeffrey Lipitz
(74) *Attorney, Agent, or Firm* — Harness, Dickey (57) ABSTRACT

A method and apparatus for providing an unsterilized item to a sterile field is disclosed. The item can include a human input device. The sterile field can be in an operating room.

27 Claims, 4 Drawing Sheets

(56) References Cited

U.S. PATENT DOCUMENTS

| | | |
|---|---|---|
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | DiMarco |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckmann et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Öberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,013 A | 7/1991 | Kramer |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |

(56) References Cited

U.S. PATENT DOCUMENTS

| | | |
|---|---|---|
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Müller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,484,437 A | 1/1996 | Michelson |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,109 A | 11/1996 | Bertagnoli |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |

(56) References Cited

U.S. PATENT DOCUMENTS

| | | |
|---|---|---|
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins |
| 5,715,836 A | 2/1998 | Kliegis et al. |
| 5,715,943 A | 2/1998 | Thompson, Jr. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polyani |
| 5,767,669 A | 6/1998 | Hansen et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,772,661 A | 6/1998 | Michelson |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,812,188 A * | 9/1998 | Adair .............................. 348/77 |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,957,844 A | 9/1999 | Dekel et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |

(56) References Cited

U.S. PATENT DOCUMENTS

| | | | |
|---|---|---|---|
| 6,076,008 | A | 6/2000 | Bucholz |
| 6,096,050 | A | 8/2000 | Audette |
| 6,104,944 | A | 8/2000 | Martinelli |
| 6,118,845 | A | 9/2000 | Simon et al. |
| 6,122,538 | A | 9/2000 | Sliwa, Jr. et al. |
| 6,122,541 | A | 9/2000 | Cosman et al. |
| 6,131,396 | A | 10/2000 | Duerr et al. |
| 6,139,183 | A | 10/2000 | Graumann |
| 6,147,480 | A | 11/2000 | Osadchy et al. |
| 6,149,592 | A | 11/2000 | Yanof et al. |
| 6,156,067 | A | 12/2000 | Bryan et al. |
| 6,161,032 | A | 12/2000 | Acker |
| 6,165,181 | A | 12/2000 | Heilbrun et al. |
| 6,167,296 | A | 12/2000 | Shahidi |
| 6,172,499 | B1 | 1/2001 | Ashe |
| 6,175,756 | B1 | 1/2001 | Ferre et al. |
| 6,178,345 | B1 | 1/2001 | Vilsmeier et al. |
| 6,194,639 | B1 | 2/2001 | Botella et al. |
| 6,201,387 | B1 | 3/2001 | Govari |
| 6,203,497 | B1 | 3/2001 | Dekel et al. |
| 6,211,666 | B1 | 4/2001 | Acker |
| 6,223,067 | B1 | 4/2001 | Vilsmeier |
| 6,233,476 | B1 | 5/2001 | Strommer et al. |
| 6,246,231 | B1 | 6/2001 | Ashe |
| 6,259,942 | B1 | 7/2001 | Westermann et al. |
| 6,273,608 | B1 | 8/2001 | Ward, Jr. et al. |
| 6,273,896 | B1 | 8/2001 | Franck et al. |
| 6,285,902 | B1 | 9/2001 | Kienzle, III et al. |
| 6,298,262 | B1 | 10/2001 | Franck et al. |
| 6,314,310 | B1 | 11/2001 | Ben-Haim et al. |
| 6,328,082 | B1 | 12/2001 | Lafond et al. |
| 6,332,089 | B1 | 12/2001 | Acker et al. |
| 6,341,231 | B1 | 1/2002 | Ferre et al. |
| 6,348,058 | B1 | 2/2002 | Melkent et al. |
| 6,351,659 | B1 | 2/2002 | Vilsmeier |
| 6,381,485 | B1 | 4/2002 | Hunter et al. |
| 6,424,856 | B1 | 7/2002 | Vilsmeier et al. |
| 6,427,314 | B1 | 8/2002 | Acker |
| 6,428,547 | B1 | 8/2002 | Vilsmeier et al. |
| 6,434,415 | B1 | 8/2002 | Foley et al. |
| 6,437,567 | B1 | 8/2002 | Schenck et al. |
| 6,445,943 | B1 | 9/2002 | Ferre et al. |
| 6,470,207 | B1 | 10/2002 | Simon et al. |
| 6,474,341 | B1 | 11/2002 | Hunter et al. |
| 6,478,802 | B2 | 11/2002 | Kienzle, III et al. |
| 6,484,049 | B1 | 11/2002 | Seeley et al. |
| 6,490,475 | B1 | 12/2002 | Seeley et al. |
| 6,493,573 | B1 | 12/2002 | Martinelli et al. |
| 6,498,944 | B1 | 12/2002 | Ben-Haim et al. |
| 6,499,488 | B1 | 12/2002 | Hunter et al. |
| 6,516,046 | B1 | 2/2003 | Fröhlich et al. |
| 6,527,443 | B1 | 3/2003 | Vilsmeier et al. |
| 6,527,444 | B1 | 3/2003 | Buchman |
| 6,551,325 | B2 | 4/2003 | Neubauer et al. |
| 6,575,202 | B2 | 6/2003 | Lafond et al. |
| 6,584,174 | B2 | 6/2003 | Schubert et al. |
| 6,609,022 | B2 | 8/2003 | Vilsmeier et al. |
| 6,611,700 | B1 | 8/2003 | Vilsmeier et al. |
| 6,640,128 | B2 | 10/2003 | Vilsmeier et al. |
| 6,694,162 | B2 | 2/2004 | Hartlep |
| 6,701,179 | B1 | 3/2004 | Martinelli et al. |
| 6,817,470 | B1 | 11/2004 | Goldberg |
| 7,311,441 | B2 | 12/2007 | Weaver et al. |
| 7,850,664 | B1* | 12/2010 | Pruter ............... 604/263 |
| 2001/0007918 | A1 | 7/2001 | Vilsmeier et al. |
| 2002/0095081 | A1 | 7/2002 | Vilsmeier |
| 2002/0151848 | A1 | 10/2002 | Capote et al. |
| 2004/0024309 | A1 | 2/2004 | Ferre et al. |
| 2004/0140028 | A1* | 7/2004 | Clark et al. ............. 150/154 |
| 2004/0261803 | A1* | 12/2004 | Boland ................. 131/231 |
| 2006/0131190 | A1 | 6/2006 | Weaver et al. |

FOREIGN PATENT DOCUMENTS

| | | |
|---|---|---|
| DE | 3042343 A1 | 6/1982 |
| DE | 35 08730 | 3/1985 |
| DE | 37 17 871 | 5/1987 |
| DE | 38 38011 | 11/1988 |
| DE | 3831278 A1 | 3/1989 |
| DE | 42 13 426 | 4/1992 |
| DE | 42 25 112 | 7/1992 |
| DE | 9306676.7 | 9/1993 |
| DE | 4233978 C1 | 4/1994 |
| DE | 197 15 202 | 4/1997 |
| DE | 197 47 427 | 10/1997 |
| DE | 197 51 761 | 11/1997 |
| DE | 198 32 296 | 7/1998 |
| DE | 20116368 | 1/2002 |
| DE | 10085137 | 11/2002 |
| EP | 0 062 941 | 3/1982 |
| EP | 0 119 660 | 9/1984 |
| EP | 0 155 857 | 1/1985 |
| EP | 0319844 A1 | 1/1988 |
| EP | 0 326 768 | 12/1988 |
| EP | 0419729 A1 | 9/1989 |
| EP | 0350996 A1 | 1/1990 |
| EP | 0651968 A1 | 8/1990 |
| EP | 0 427 358 | 10/1990 |
| EP | 0 456 103 | 5/1991 |
| EP | 0581704 B1 | 7/1993 |
| EP | 0655138 B1 | 8/1993 |
| EP | 0894473 A2 | 1/1995 |
| EP | 0469966 | 8/1995 |
| EP | 0 908 146 | 10/1998 |
| EP | 0 930 046 | 10/1998 |
| FR | 2417970 | 2/1979 |
| FR | 2 618 211 | 7/1987 |
| GB | 2 094 590 | 2/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 6/1998 |
| WO | WO 88/09151 | 12/1988 |
| WO | WO 89/05123 | 6/1989 |
| WO | WO 90/05494 | 5/1990 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 95/07055 | 3/1995 |
| WO | WO 96/11624 | 4/1996 |
| WO | WO 96/32059 | 10/1996 |
| WO | WO 97/49453 | 6/1997 |
| WO | WO 97/36192 | 10/1997 |
| WO | WO-9802107 | 1/1998 |
| WO | WO 98/08554 | 3/1998 |
| WO | WO 98/38908 | 9/1998 |
| WO | WO 99/38449 | 1/1999 |
| WO | WO 99/15097 | 4/1999 |
| WO | WO 99/52094 | 4/1999 |
| WO | WO 99/21498 | 5/1999 |
| WO | WO 99/23956 | 5/1999 |
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/37208 | 7/1999 |
| WO | WO 99/60939 | 12/1999 |
| WO | WO 01/30437 A1 | 5/2001 |

OTHER PUBLICATIONS

Adams et al., "Orientation Aid for Head and Neck Surgeons," Innov. Tech. Biol. Med., vol. 13, No. 4, 1992, pp. 409-424.

Barrick et al., "Prophylactic Intramedullary Fixation of the Tibia for (56) References Cited

OTHER PUBLICATIONS

Stress Fracture in a Professional Athlete," Journal of Orthopaedic Trauma, vol. 6, No. 2, pp. 241-244 (1992).
Barrick et al., "Technical Difficulties with the Brooker-Wills Nail in Acute Fractures of the Femur," Journal of Orthopaedic Trauma, vol. 4, No. 2, pp. 144-150 (1990).
Barrick, "Distal Locking Screw Insertion Using a Cannulated Drill Bit: Technical Note," Journal of Orthopaedic Trauma, vol. 7, No. 3, 1993, pp. 248-251.
Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.
Benzel et al., "Magnetic Source Imaging: a Review of the Magnes System of Biomagnetic Technologies Incorporated," Neurosurgery, vol. 33, No. 2 (Aug. 1993), pp. 252-259.
Bergstrom et al. Stereotaxic Computed Tomography, Am. J. Roentgenol, vol. 127 pp. 167-170 (1976).
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.
Brown, R., M.D., A Stereotactic Head Frame for Use with CT Body Scanners, Investigative Radiology © J.B. Lippincott Company, pp. 300-304 (Jul.-Aug. 1979).
Bryan, "Bryan Cervical Disc System Single Level Surgical Technique", Spinal Dynamics, 2002, pp. 1-33.
Bucholz et al., "Variables affecting the accuracy of stereotactic localizationusing computerized tomography," Journal of Neurosurgery, vol. 79, Nov. 1993, pp. 667-673.
Bucholz, R.D., et al. Image-guided surgical techniques for infections and trauma of the central nervous system, Neurosurg. Clinics of N.A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D., et al., Intraoperative Ultrasonic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).
Champleboux et al., "Accurate Calibration of Cameras and Range Imaging Sensors: the NPBS Method," IEEE International Conference on Robotics and Automation, Nice, France, May 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Cutting M.D. et al., Optical Tracking of Bone Fragments During Craniofacial Surgery, Second Annual International Symposium on Medical Robotics and Computer Assisted Surgery, pp. 221-225, (Nov. 1995).
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance for the Spine Surgeon," Spinal Frontiers, Apr. 1996, pp. 7-9.
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., et al., Interactive Image-Guided Neurosurgery, IEEE Trans. on Biomed. Eng., vol. 89, No. 12, pp. 1226-1231 (1992).
Galloway, R.L., Jr. et al, Optical localization for interactive, image-guided neurosurgery, SPIE, vol. 2164, pp. 137-145 (undated.
Germano, "Instrumentation, Technique and Technology", Neurosurgery, vol. 37, No. 2, Aug. 1995, pp. 348-350.
Gildenberg et al., "Calculation of Stereotactic Coordinates from the Computed Tomographic Scan," Neurosurgery, vol. 10, No. 5, May 1982, pp. 580-586.
Gomez, C.R., et al., Transcranial Doppler Ultrasound Following Closed Head Injury: Vasospasm or Vasoparalysis?, Surg. Neurol., vol. 35, pp. 30-35 (1991).
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. 1996, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).
Gueziec et al., "Registration of Computed Tomography Data to a Surgical Robot Using Fluoroscopy: A Feasibility Study," Computer Science/Mathematics, Sep. 27, 1996, 6 pages.
Guthrie, B.L., Graphic-Interactive Cranial Surgery: The Operating Arm System, Handbook of Stereotaxy Using the CRW Apparatus, Chapter 13, pp. 193-211 (undated.
Hamadeh et al, "Kinematic Study of Lumbar Spine Using Functional Radiographies and 3D/2D Registration," TIMC UMR 5525—IMAG.
Hamadeh et al., "Automated 3-Dimensional Computed Tomographic and Fluoroscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Hatch, "Reference-Display System for the Integration of CT Scanning and the Operating Microscope," Thesis, Thayer School of Engineering, Oct. 1984, pp. 1-189.
Hatch, et al., "Reference-Display System for the Integration of CT Scanning and the Operating Microscope", Proceedings of the Eleventh Annual Northeast Bioengineering Conference, Mar. 14-15, 1985, pp. 252-254.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

(56) References Cited

OTHER PUBLICATIONS

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Joskowicz et al., "Computer-Aided Image-Guided Bone Fracture Surgery: Concept and Implementation," CAR '98, pp. 710-715.
Kali, B., The Impact of Computer and Imgaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored $CO_2$ Laser," Acta Neurochirurgica, vol. 68, 1983, pp. 1-9.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., Long-Term Experience with Different Types of Localization Systems in Skull-Base Surgery, Ear, Nose & Throat Surgery, Chapter 51, pp. 635-638 (undated).
Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Computer Assisted Spine Surgery: A Technique for Accurate Transpedicular Screw Fixation Using CT Data and a 3-D Optical Localizer," TIMC, Faculte de Medecine de Grenoble.
Lavallee et al., "Image guided operating robot: a clinical application in stereotactic neurosurgery," Proceedings of the 1992 IEEE International Conference on Robotics and Automation, May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.
Lavallee, "VI Adaption de la Methodologie a Quelques Applications Cliniques," Chapitre VI, pp. 133-148.
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.
Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Merloz, et al., "Computer Assisted Spine Surgery", Clinical Assisted Spine Surgery, No. 337, pp. 86-96.
Ng, W.S. et al., Robotic Surgery—A First-Hand Experience in Transurethral Resection of the Prostate Surgery, IEEE Eng. In Med. and Biology, pp. 120-125 (Mar. 1993).
Pelizzari et al., "Accurate Three-Dimensional Registration of CT, PET, and/or MR Images of the Brain," Journal of Computer Assisted Tomography, Jan./Feb. 1989, pp. 20-26.
Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.
Penn, R.D., et al., Stereotactic Surgery with Image Processing of Computerized Tomographic Scans, Neurosurgery, vol. 3, No. 2, pp. 157-163 (Sep.-Oct. 1978).
Phillips et al., "Image Guided Orthopaedic Surgery Design and Analysis," Trans Inst. MC, vol. 17, No. 5, 1995, pp. 251-264.

(56) References Cited

OTHER PUBLICATIONS

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Prestige Cervical Disc System Surgical Technique, 12 pgs.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurg, vol. 79, pp. 296-303 (Aug. 1993).

The Laitinen Stereotactic System, E2-E6.

Thompson, et al., A System for Anatomical and Functional Mapping of the Human Thalamus, Computers and Biomedical Research, vol. 10, pp. 9-24 (1977).

Trobaugh, J.W., et al., Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," pp. 119-128.

"The Power of Selection," CFI Medical Solutions brochure, Contour Fabricators, Inc., 2006 (pp. 1-42).

"The Power of Selection," Performance Plus™ brochure, Contour Fabricators, Inc. 2005 (6 pages).

International Preliminary Report on Patentability mailed Apr. 23, 2008.

International Search Report and Written Opinion for PCT/US/2007/001111 mailed May 10, 2007, claiming benefit of U.S. Appl. No. 11/334,798, filed Jan. 18, 2006.

\* cited by examiner

METHOD AND APPARATUS FOR PROVIDING A CONTAINER TO A STERILE ENVIRONMENT

FIELD

The present disclosure is directed to a method and apparatus for maintaining a sterile environment, and particularly to a method and apparatus for maintaining a sterile environment around a computer input device.

BACKGROUND

The statements in this section merely provide background information related to the present disclosure and may not constitute prior art.

Computer and/or processor systems have become ubiquitous in modern society and times. Computer systems can be used for various applications, such as data storage, data manipulation, data creation and the like. Computer systems generally have human interface portions, such as human input portions and human readable output portions. The various portions of the computer system can be used in various applications, such as in design, program execution, and the like. For example, a computer system can be used in a computer assisted surgical system, such as those disclosed U.S. patent application Ser. No. 10/976,328 filed Oct. 28, 2004, entitled "Method and Apparatus for Calibrating Non-Linear Instruments", incorporated herein by reference.

Computer assisted surgical procedures can include various neurological, spinal, and the like procedures that require a very precise navigation of instruments to safely perform the surgical procedure. Nevertheless, it may be desirable to perform the procedure through a substantially small incision to reduce recovery time, increase efficacy of the procedure, and other appropriate reasons. Therefore, computer systems can assist in navigating, such as tracking an anatomical portion or a surgical instrument, relative to a patient.

The computer systems, therefore, are generally required in operating rooms near a patient. Operating rooms, at least during a surgical procedure, are generally maintained in a substantially sterile state to reduce the possibility of infection of a patient. Computer systems, therefore, are generally required to be kept away from a substantially sterile field, due to the difficulty of sterilizing various portions of the computer system. Although various portions of the computer system may be covered to maintain a sterile and secure environment, such as the human readable output display. The various input portions, however, are nearly impossible to put into a sterile field because of the human interaction required with them. For example, it may be desirable to input data or instructions during a surgical procedure, therefore requiring that the input device either be sterile or removed from the sterile field.

Therefore, it may be desirable to provide a system and apparatus that can allow for maintaining a sterile field around a human input device, such as a keyboard, a mouse, a trackball, or the like, to assist in allowing a surgeon or user more precise control of a computer system.

SUMMARY

An apparatus and method for providing a sterile field around a human input device, such as the keyboard, mouse, trackball, stylus, or the like is disclosed. Generally, the system or apparatus allows for positioning a human input device within a container that is sterile on the exterior of the container so that the human input device can be moved into a sterile field. For example, a human input device can be positioned within a sterile container in a non-sterile area. The container can then be moved with the human input device therein from the non-sterile area to the sterile area.

According to various embodiments a system for providing a substantially sterile item to a sterile field is disclosed. The system can include a container operable to contain the item and a closure system operable to close the container to an ambient environment. The container can have an exterior wall to define an internal portion where the item is operable to be positioned within the interior portion. The item is operable to be positioned within the container during an operative procedure to move the item into a sterile field without sterilizing the item.

According to various embodiments a method of providing a member to a sterile field in an operating room is disclosed. The method can include providing a container operable by a user in an operating room to contain the member and moving the member into the container. The container can be closed to an ambient atmosphere after moving the member into the container. The member can also be used to provide input to a system after the member is in the container.

According to various embodiments a method of using an unsterilized human input device with a processor in or near a sterile field is disclosed. The method can include providing a container having a sterile exterior and moving the human input device into the container while maintaining the sterility of the exterior of the container. The container can be closed to substantially completely contain the human input device within the provided container. The human input device can be used within a sterile field while maintaining the sterile field.

According to various embodiments a method of using a computer assisted surgical navigation system is disclosed. The method of using the system can include providing a navigation system to track a tracking sensor. A container to contain a human input device is provided and the human input device can be put in the in the provided container. The sterility of an exterior of the provided container can be maintained in part by closing the container to an exterior environment.

Further areas of applicability will become apparent from the description provided herein. It should be understood that the description and specific examples are intended for purposes of illustration only and are not intended to limit the scope of the present disclosure.

BRIEF DESCRIPTION OF THE FIGURES

The figures described herein are for illustration purposes only and are not intended to limit the scope of the present disclosure in any way.

DETAILED DESCRIPTION OF VARIOUS EMBODIMENTS

The following description is merely exemplary in nature and is not intended to limit the present disclosure, application, or uses.

A human input device can be any appropriate device, such as those generally known in the art, and those that can be in the future created. Various examples include a mouse, a keyboard, a pointer, a stylus, a foot pedal, and the like. Nevertheless, the human input device can be formed in such a manner that it may not be sterilized using generally known sterilization techniques, such as an autoclave, chemical sterilization, radioactive sterilization, or the like. To allow the human input device be used in a sterile field the human input device can be positioned within a container that allows for the maintaining and creation of a sterile field around the human input device. The container can be formed to allow contact or the use of the human input device. Although various human input devices can be used, a mouse is illustrated herein merely for exemplary purposes. Further, it will be understood that various input devices can be hardwired or transmit wirelessly to a computer system. Therefore, a wireless mouse is illustrated here merely for exemplary purposes. It will also be understood that a human readable output device can be positioned within a container, as disclosed herein. Thus, although a human input device is discussed other items, such as a monitor, printer, heads up display and the like, can be put in a container.

Figure 1:
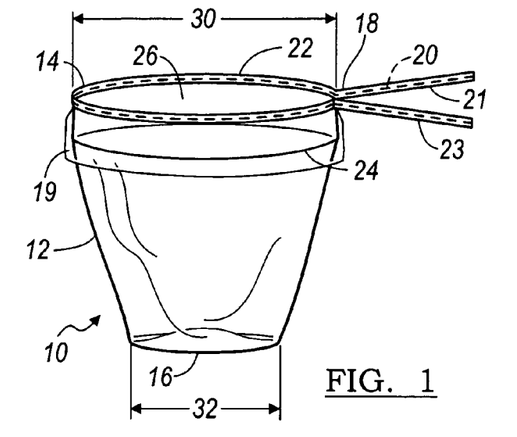
FIG. 1 is a plan view of a sterile container according to various embodiments.

With reference to FIG. 1, a sterile container 10 is illustrated. The sterile container 10 can include various portions, such as an outer wall 12, an upper portion 14 that can define an opening and a lower portion 16 that can define a closed end or a second opening. It may be selected that only a single end of the container 10 includes an opening for ease of use of the sterile container 10. Further, the various portions of the container 10 can include a closing mechanism 18. A handle portion 19 can also be provided. The handles 19 can be formed as a part of the container as a single member 19 or integrated with the container at a selected time. The handle 19 can also act as a member to protect a user, such as a sterile user, from contamination from the human input device or non-sterile user. Thus, it will be understood that that the handle 19 can be both a grasping member and a protective member.

The closing mechanism 18 can be any appropriate closing mechanism, including those described herein and exemplarily illustrated in FIG. 1. For example, a closing mechanism 18 can include a deformable member, such as a wire 20. The wire 20 can be formed inside of a band portion 22 that is also a portion of the closing apparatus 18. The wire 20 can be selectively deformed to maintain a lock or closure of the container 10. The band and wire can terminate in two ends 21, 23 for use by a user to complete the closure.

The container 10 can further include various demarcations, such as a scoring or folding line 24. The scoring or folding line 24 can also be a sterilization insurance mark to insure that an appropriate portion of the container 10 has been closed to maintain or create a seal between an interior of the container 26 and an ambient or exterior environment. It will be understood that the demarcation line 24 is not required relative to the container and is optional for assisting a user.

As discussed further herein, once a device, such as a human input device, is positioned within the container 10, the upper portion 14 can be closed and the upper portion of the container 14 can be rolled over on itself and the closure device 18 used to maintain the rolls. The demarcation line 24, which is optional, can be provided to insure that appropriate number of rolls have been created to create a substantially complete seal between the interior of the bag 26 and an exterior ambient environment.

The container 10 can further include a selected dimension. For example, the upper portion of the bag 14 can include a dimension 30 that is greater than a dimension 32 of a lower portion of the bag 16. The dimension 30 can be provided to allow for easy insertion or access to the interior of the container 26 with a device, such as a human input device. The dimensions 30, 32 can be any appropriate dimension, but can form the container into a substantially trapezoidal shape. The shape and dimensions of the container 10 can be provided so that once the human input device is positioned within the container 10 the amount of material around the human input device is substantially reduced or minimized.

The container 10 can be formed of any appropriate material. For example, a polymer material can be used to form the container 10, as long as the polymer is substantially air, gas, particle, tight. Any other appropriate materials can be used, such as alloys, the combination of polymers and metal alloys, natural fibers, or any appropriate materials. Nevertheless, it may be selected that the exterior wall 12 of the container 10 is substantially flexible and malleable so that the container 10 can be fitted around or formed substantially to the shape and size of a human input device. Also, the container 10, according to various embodiments, can be formed to be substantially clear or transparent, allowing a user to see an item within the container. The container 10 can be formed to allow a fine tactile discrimination of an item in the container. This can allow for ease of use of an item placed within the container.

Figure 2:
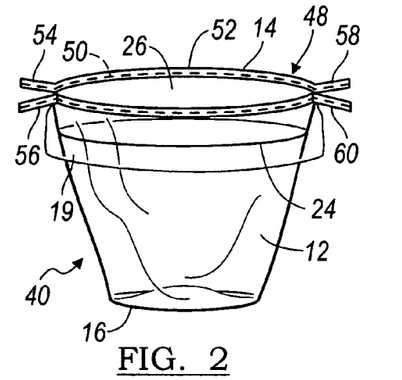
FIG. 2 is a perspective view of a sterile container according to various embodiments.

With reference to FIG. 2, a sterile container 40 is illustrated. Similar portions of the sterile container 40 that are similar to the portions of the sterile container 10 will be indicated with similar reference numerals. The sterile container 40 can include the exterior wall 12, a bottom portion 16, and a top portion 14. Further, a marking line or sterilization line 24 can also be provided on the outer wall. The handle 19 can also be provided on the container 40.

The sterile container 40 can also be formed as substantially similar materials to the sterile container 10 such as those discussed above. Although the material for forming a sterile container 40 can be provided in any appropriate manner, it can include substantially airtight or non-permeable polymers, alloy materials, or the like. The materials can also allow for maintaining a sterile environment within the container once it is closed.

The sterile container 40 can also include a closure system 48. The closure system 48 can include a wire 50 that is enclosed within a band 52. The closure system 48, however, can include a first set of closing tabs 54, 56 and a second set of closing tabs 58, 60. The closing tabs 54-60 can be used in a manner similar to the closing tabs 21, 23 of the closing system 18. As discussed above, a human input device can be positioned within the interior 26 of the container 40 and the closing device 48 be used to close the upper portion 14 of the container 40. The closing tabs 54-60 can then be used to ensure that the closure system 48 remains closed. The tabs 54-60 can be crimped, as discussed further herein, to maintain the sterile closure.

Figure 3:
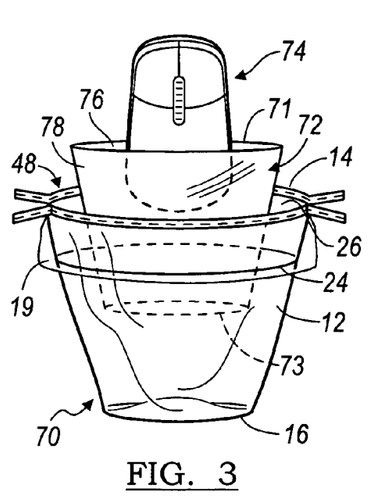
FIG. 3 is a perspective view of a sterile container and human input device according to various embodiments.

With reference to FIG. 3, a sterile field maintenance container 70 is illustrated. Portions of the container 70 that are similar to the portions described above will be referenced with similar reference numerals. The container 70 can include an exterior wall 12, a bottom portion 16, an upper portion 14, and the closure line 24. The container 70 can further include a closure system similar to the closure system 48 discussed above. The container 70 can also include any appropriate shape, including those discussed above, such as a trapezoidal shape, a square shape, round shape, or the like. The container 70 can also include the handle 19.

The sterile container system 70, however, can also include additional portions, which also can be included in the various embodiments, even those discussed herein, even if only illustrated in FIG. 3. An additional transfer or positioning portion 72 can be provided with the container 70. The sterile transfer portion 72 can assist in moving a human input device 74 from an exterior or ambient environment to the interior 26 of the container 70. The transfer portion 72 can include an interior portion 76 and an exterior portion 78. The transfer sleeve 72 can be provided within the container 70 and accessed by a substantially sterilized user or portion. The user can pull the transfer portion 72 partially out of the container 70, to allow the human input device 74 to be moved into the container 70 while reducing the possibility of touching a portion of the container 70 with the user input device 74 or by a user moving the user input device 74. A method of moving the human input device 74 is exemplary discussed further herein.

Figure 4:
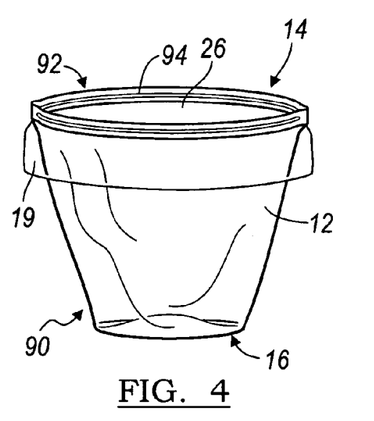
FIG. 4 is a perspective view of a sterile container according to various embodiments.

With reference to FIG. 4, a sterile container 90 is illustrated. The sterile container 90 can include similar portions to those discussed above, where like reference numerals reference the like portions. For example, the sterile container 90 can include an exterior wall 12, an upper portion 14, and a lower portion 16. Further, the sterile container 90 can be formed of material similar to those discussed above, include a shape similar to those discussed above, or be formed of any appropriate material or shape. The container 90 may also include the handle 19.

The sterile container 90 can include a closure system 92 that can be provided in any appropriate manner. For example, the closure system 92 can include a closing or sealing mechanism 94. The sealing mechanism 94 can be any appropriate sealing mechanism such as a rail and groove interlocking or engagement system. The interlocking closure system can be used in a generally known, on various devices such as closure containers sold by Ziploc®. A single, double, triple, or any appropriate number can be used to lock the closure system 92 to create a seal between an exterior or ambient environment and the interior 26 of the container 90. Further, various adhesives can be used as a part of the closure system 92 to adhere portions of the upper portion 14 together to create a substantially airtight seal. Also, two portions of the container 90 can be welded, such as melt welded, together to seal the container.

It will be understood, therefore, that any appropriate closure mechanism can be provided to close a sterile container relative to an external or ambient environment. The closure mechanism can be provided to substantially minimize or eliminate the transfer of any ambient or exterior contaminant into an interior of the container according to various embodiments. Although the human input device, that is substantially not sterile, can be positioned within the container, the entire container can then be moved into a sterile field where the human input device can be used regardless that it is surrounded by the container. The fine tactile sensations can allow a user, such as a physician, can directly access a computer system with the human input device without requiring a human or secondary user to input instructions, commands, information or the like into a computer system. Further, the containers can be substantially disposable, single use, or a combination thereof.

With reference to FIGS. 5A-5F, a method of using the sterile container 70 is illustrated. Although the use of the sterile container 70 is illustrated in FIGS. 5A-5F, it will be understood that a sterile container, according to any of the various embodiments, can be used according to the exemplary method described herein.

Figure 5A:
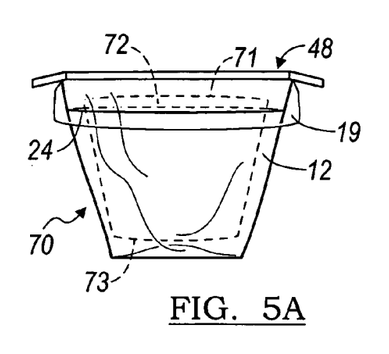
FIGS. 5A-5F illustrate a sterile container according to various embodiments and a method of positioning a human input device in a sterile container according to various embodiments.

With initial reference to FIG. 5A, as discussed above, the sterile container 70 includes an exterior wall 12 and a closure mechanism 48. Contained within the container 70 is the optional transfer sleeve 72. As discussed above, the transfer sleeve can include a first end 71 that can be substantially open and a second end 73 that can also be substantially open. The two ends 71, 73 can assist in allowing the passing of the human input device 74 from an exterior environment to the interior 26 of the container 70.

Figure 5B:
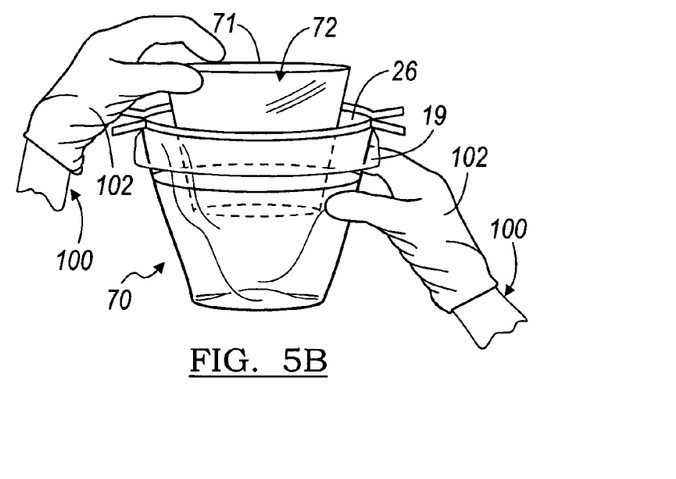

With additional reference to FIG. 5B, a substantially sterile user 100 can be sterilized according to any appropriate system, such as with chemicals and other appropriate sterilization techniques and can be covered, such as with a sterile glove 102. The user 100 can contact the container 70 without destroying the sterile field of the container 70 due to the sterilization of the user 100. Thus, the user 100 can obtain access to the interior 26 of the container 70 and partially remove the transfer sleeve 72 to allow for access to the first end 71 of the transfer sleeve 72. For example, the user 100 can use the handle 19 to manipulate the container 70 to obtain access to the container 70 or to hold the opening of the container open.

Figure 5C:
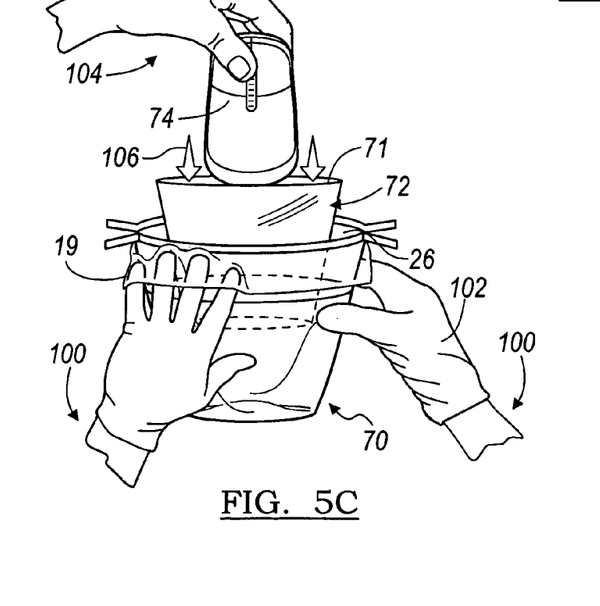

With additional reference to FIG. 5C, a non-sterile user 104 can position the human input device 74 relative to the first end 71 of the transfer sleeve 72. The user 104 can be substantially non-sterile and move the human input device 74 relative to container 70 because of the transfer sleeve 72. The transfer sleeve is substantially sterile because it has been maintained or included with the sterile container 70 or the sleeve 72 can be non-sterile. Therefore, the sterile sleeve 72 can also be touched by the non-sterile user 104, at least on an exterior portion thereof, to allow for assisting in moving the human input device 74 into the interior 76 of the container 70. The sterile user 100 can use the handle to hold the container 70 in a selected position, or any other appropriate portion of the container 70.

The container 70 can also be held by the user 100 to allow access to the sleeve 72 by the user 104. The user 104 can contact and manipulate the sleeve 72 without contaminating the exterior of the container 70 if the user 100 appropriately holds the container 70. This can assist in moving the human input device into the container 70 without contaminating an exterior thereof so that it can be moved into the sterile field once the container 70 is sealed. Thus, it will be understood, that the sleeve 72 can be accessed by either user 100 or 104 to assist in moving the human input device into the container 70.

As discussed above the sterile user 100 can use the handles 19 to cover a portion of the user 100 to reduce possible contamination of the sterile user 100 by the human input device 74 or the non-sterile user 104. Thus, the handle 19 can be both an assistant member in holding and manipulating the container 70 but also a protective member in reducing the possibility of contamination. It will be understood, therefore, that the handle 19 can be formed of any appropriate material or be any appropriate size to assist in either manipulating the container 70 or protecting the user 100 or the exterior of the container 70 from contamination.

Figure 5D:
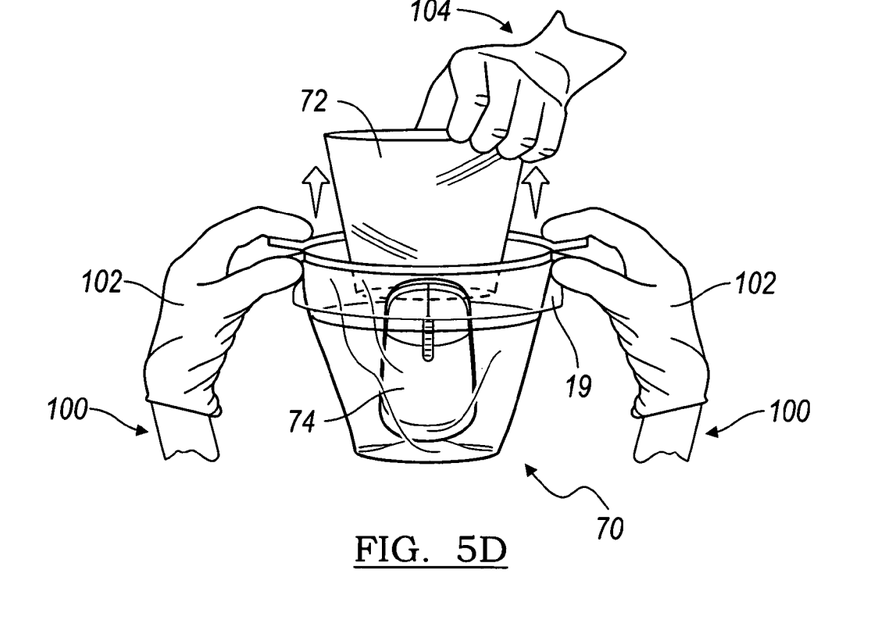

Once the human input device 74 has been positioned relative to the sleeve 72, the human input device 74 can be substantially released to allow it to move in the direction of gravity, which is generally illustrated in the direction of arrows 106. Therefore, the human input device 74 can pass through the sleeve 72 and into the container 70 as illustrated in FIG. 5D. Because the human input device 74 has passed into the bag container 70, the sleeve 72 can be removed by the non-sterile user 104 while the human input device 74 is within the container 70. The container 70 is substantially sterile on an exterior portion thereof and reduces the potential or does not allow for passage of any contaminants that may be on the human input device 74 to an exterior of the container 70. Similarly, portions that are exterior to the container 70 can be maintained on the exterior portion and not allowed to enter the container 70.

Figure 5E:
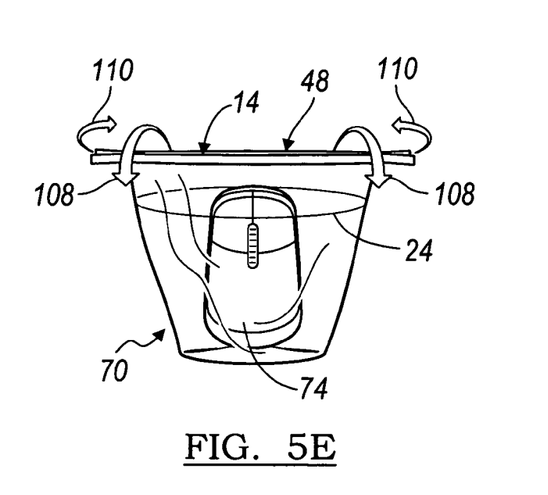

With reference to FIG. 5E, once the human input device 74 is positioned within the container 70, the closure mechanism 48 can be operated by the sterile user 100 to close the container 70. As illustrated, the closure device 48 and a portion of the upper portion 14 of the container 70 can be rolled generally in the direction of arrows 108 to create folds out the upper portion of the container 14. As discussed above, the sterilization or closing mark 24 can be used to ensure that enough of the container 70 has been closed or used to form an appropriate seal. It will be understood that rolling the upper portion of the container 70 can create a substantially convoluted or circuitous seal substantially so that no contaminants can move between the interior 26 of the container 70 or the exterior of the container 70. Also, if the optional handles 19 are provided they can be rolled inside the rolls formed to assist in assuring that no contamination occurs or in reducing the possibility of contamination. The handle 19 inside the roll can reduce the possibility of contamination on the exterior of the container 70.

Figure 5F:
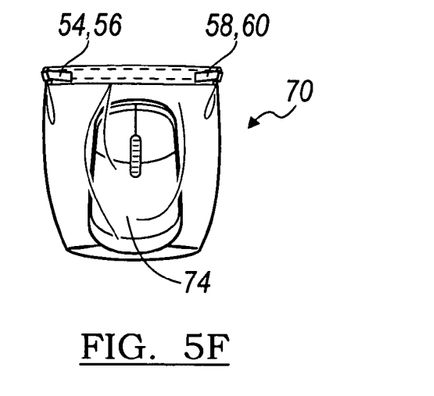

With reference to FIG. 5F, the tabs 54-60 can then be folded over to maintain the seal of the container 70. The tabs 54-60 can be used to ensure that the seal formed by rolling the portion of the bag is maintained during use of the human input device 74. The tabs 54-60 can be folded in any appropriate manner but can generally be folded in the direction of arrows 110. Therefore, the container 70 can be provided to a substantially sterile filed in a sterile manner, such as within an operating room. Because the closure mechanism 48, or a closer mechanism according to any appropriate embodiments, defines a seal any contaminants that may be on the human input device 74 cannot escape into the sterile field. Similarly, no exterior portion, such as contaminants from an exterior field can move to an interior of the container 70.

The container 70 can be closed with the closure mechanism 48 to substantially seal the container 70. The seal formed by the closure mechanism 48 can allow the interior of the container to be sealed to an exterior environment so that a sterile field is not disturbed by the human input device 74 that has not been sterilized. The container 70 allows the human input device 70 to be moved into the sterile field. The closure mechanism 48 assists in this by creating and maintaining the substantial seal of the container 70.

It will be understood that the containers according to the various embodiments can be used in any appropriate manner to move the human input device 74 to an interior of the containers. It will be understood that the transfer sleeve 72, although illustrated here, is not necessary and the human input device can simply be dropped into the container by a user. The transfer sleeve 72 can simply be used for ease of the transfer of the human input device or for any appropriate reason.

Figure 6:
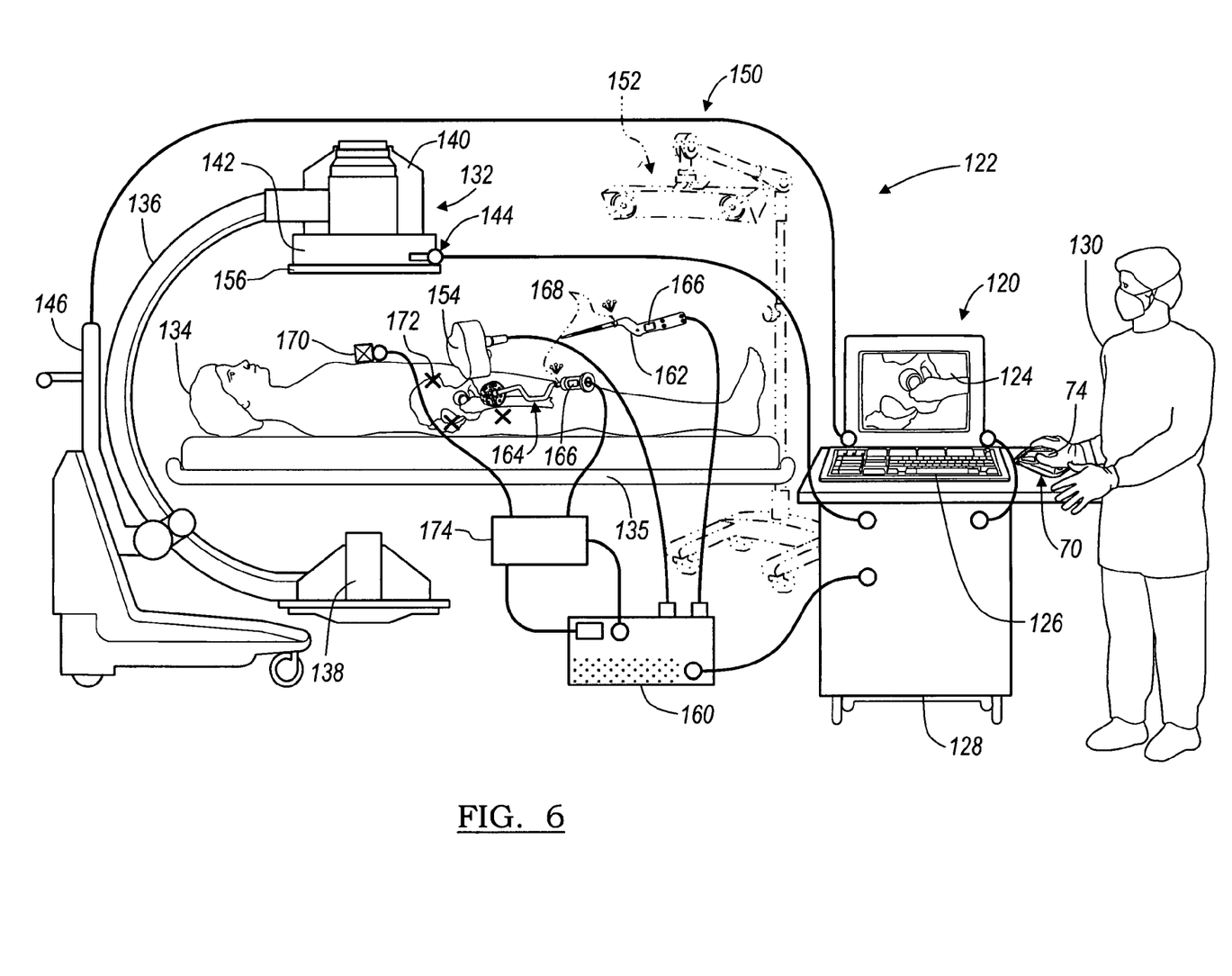
FIG. 6 illustrates a human input device positioned within a sterile container in an environmental view.

With reference to FIG. 6, the contained human input device 74 can then be provided into and in a sterile field, such as to provide input to a computer system 120. The computer system 120 can be any appropriate computer system such as the computer system described in U.S. patent application Ser. No. 10/976,328 filed Oct. 28, 2004, entitled "Method and Apparatus for Calibrating Non-Linear Instruments", incorporated herein by reference.

The computer system 120 can be a part of a work station and part of a larger navigation system 122. The computer 120 or the work station 120 can also include a human readable device 124, such as a monitor. Also, as discussed above, other human input devices such as a keyboard 126 can also be provided. The work station 120 can be included on a moveable cart or station 128. As discussed above, the human input device 74 can be enclosed in the container 70 and be used with the computer system 120 to assist in inputting information, such as locations, distances, instrument types and the like.

As discussed above, a person that is within the sterile field, such as a user including a surgeon 130, can contact the container 70 without fear of breaking or severing the sterile field. Because the container 70 is sterile and the human input device 74 is contained within the container 70, the user 130, who is also sterile, can manipulate the user input device 74 without fear of destroying the sterile field. Therefore, the container 70 can allow for direct input by a user, such as the surgeon, into the computer system 120 to assist in the procedure, such as one using a navigation system 122.

The navigation system 122 can be any appropriate navigation system such as the navigation system disclosed in U.S. patent application Ser. No. 10/976,328 filed Oct. 28, 2004, entitled "Method and Apparatus for Calibrating Non-Linear Instruments", incorporated herein by reference. Therefore, portions of the navigation system 122 will be listed briefly but not described in detail.

The navigation system 122 can include various portions, such as an imaging device 132 that can be positioned relative to a patient 134. The patient can be supported on a patient support 135, which can include a bed or other structure. The imaging device 132 can be any appropriate imaging device, such as a C-arm 136. The C-arm 136 can include an x-ray source 138 and a receiving section 140. The receiving section can include or be used with a tracking target 142. Further, radiation sensors 144 can be provided for various purposes, such as determining when imaging is occurring. The C-arm 136 can be controlled with a C-arm controller 146 that can be interconnected with the work station 120 using any appropriate mechanism.

The image created by the imaging system 132 can be displayed on the display 124 or any appropriate display portion. Further, the images can be used with the navigation system 122 and a tracking system 150. The tracking system 150 can include various portions, such as an optical array or localizer 152 or a coil array or localizer 154. It will be understood that any appropriate number of localizers can be provided and any appropriate type of localizers can be provided for various navigation systems. For example, an additional localizer 156 can be provided relative to the imaging system 132. It will be understood that the localizers can be positioned in any appropriate position to assist in the navigation system 150.

A probe interface or interface system 160 can be provided to allow for an interface connection between the work station 120 and the various instruments and probes provided relative to the patient 134. For example, a navigation probe 162 can be used and tracked during an operative procedure. Further, an instrument 164, such as a reamer, can be provided. The instruments and probe 162, 164 can be provided with various tracking sensors such as electromagnetic tracking sensors 166 or optical tracking sensors 168. It will be understood that any appropriate tracking sensor can be provided and can depend upon the type of tracking system 150 being used. Further, a dynamic reference frame 170 can be provided that is interconnected with the patient 134 to allow for a dynamic reference or dynamic localization of the patient 134. Further, fiducial markers 172 can be provided to allow for an initial or re-registration of the patient 134 relative to image data. The various instruments and systems can also be passed through an isolator or circuit box 174 to assist in isolating the various instruments from the electronic components of the navigation system 122.

It will be understood that the navigation system 122 can be any appropriate navigation system and the navigation system 122 illustrated is merely exemplary. Further, the work station 120 can be any appropriate work station and the work station 120 illustrated is also merely exemplary. Nevertheless, the human input device 74 can be included within the container 70 to allow for a person within a sterile field, such as the user 130, to input information and instructions into the work station 120 without destroying the sterile field. It will be understood that the human input device 126 can also be included within an appropriate container, including those discussed that can be sized, dimensioned, and the like for various purposes. It will be understood that the above method and use of any container ins merely exemplary. The user input device 74, or any appropriate device, can be put in a container in any appropriate manner.

What is claimed is:

1. A system for delivering an item to a sterile field by a user, comprising:
    a container having an open end and a closed end, wherein the container is configured to contain the item;
    a closure system configured to close the open end of the container to an ambient environment, wherein the closure system includes a deformable member, at least a portion of the open end of the container can be wrapped about the deformable member, and the deformable member is configured to be crimped to a selected position to maintain the position of at least a portion of the open end of the container;
    the container including an exterior wall to define an internal portion where the item is operable to be positioned within the internal portion;
    wherein the container is configured to receive the item through the open end during an operative procedure to move the item into a sterile field without sterilizing the item;
    a passage system comprising a sleeve including a first open end, a second open end, and a wall extending between the first open end and the second open end, the sleeve provided within the container and configured to be pulled partially out of the container at a first time;
    wherein the sleeve having the first open end, the second open end, and the wall extending between the first open end and the second open end is removable from the container at a second time that is later than the first time when then sleeve is pulled partially out of the container; and
    a handle in addition to the closure system, wherein the handle has a flap that is connected near the closure system and extends away from the closure system towards the closed end of the container to define a volume between the exterior wall of the container and the flap and configured to be grasped by the user and protect the user from contacting the item when the item is positioned within the container, the handle comprising a part of the container.

2. The system of claim 1, wherein the container further includes an edge wall so that the container defines a first dimension near a first portion and a second greater dimension near a second portion.

3. The system of claim 2, wherein the first dimension is at an open portion of the container and the second dimension is at a closed end of the container.

4. The system of claim 2, wherein the portion of the container defining the first dimension can be operated to close the container by moving a portion of the container closer to the second portion of the container.

5. The system of claim 2, wherein the first dimension and the second dimension are operable to make the container define a trapezoidal shape.

6. The system of claim 1, wherein the closure system substantially seals an interior of the container from an exterior environment.

7. The system of claim 1, wherein said container is at least one of transparent, opaque, semi-transparent, or combinations thereof.

8. The system of claim 1, wherein the closure system includes at least one of a twist tie, a four-ended twist tie, a groove and rail interlock system, a color change system, an adhesive, or combinations thereof.

9. The system of claim 1, wherein the item includes a human input device.

10. The system of claim 9, wherein the human input device includes at least one of a mouse, a track ball, a keyboard, a stylus, a laser input member, a foot pedal, or combinations thereof.

11. The system of claim 9, wherein the human input device is operable to be positioned through the closure system and substantially surrounded by the container.

12. The system of claim 1, wherein the item comprises a portion of a surgical navigation system.

13. The system of claim 12, wherein the surgical navigation system includes at least one of a tracking system, a tracking sensor, a processor, a human readable output system, an imaging system, a surgical instrument, a dynamic reference frame, a localizer, or combinations thereof.

14. The system of claim 13, wherein the surgical navigation system includes the processor and the item is operable to provide instructions to the processor.

15. The system of claim 1, wherein the handle is coupled to the container separate and in addition to the closure system.

16. The system of claim 1, wherein the flap comprises a skirt configured about the closure system.

17. The system of claim 16, wherein the flap is connected to the container and extends in a direction away from the closure system and towards a closed end of the container, defining a covered section between the flap and the container, the covered section configured to cover a portion of the user when the handle is grasped.

18. A system for delivering an item to a sterile field by a user, comprising:
    a container configured to contain the item, the container having an open end defined by a wall and a closed end defined by the wall, wherein the wall defines an internal portion where the item is operable to be positioned within the internal portion;
    a closure system configured to close the container to an ambient environment, wherein the closure includes a deformable member;
    a handle configured to be grasped by the user and protect the user from contacting the item when the item is positioned within the container, the handle comprising a part of the container; and
    a passage system defined by a sleeve having a first open terminal end, a second open terminal end, and a wall extending between the first open terminal end and the second open terminal end, the sleeve provided within the container and configured to be pulled partially out of the container at a first time and completely removed from the container at a second time later than the first time such that the second open terminal end is removed from the container;

wherein the item is operable to pass through the sleeve at the first time from an exterior environment to the internal portion of the container and be positioned within the container during an operative procedure to move the item into a sterile field without sterilizing the item.

19. The system of claim 18, wherein the handle is coupled to the container proximate to the closure system at the open end of the container and comprises a skirt configured about the closure system, the skirt extending in a direction away from the closure system and the open end, wherein the skirt defines a covered section encompassing a volume between the flap and the container, the covered section configured to cover a portion of the user when the handle is grasped.

20. The system of claim 18, wherein the sleeve-having the first open terminal end, the second open terminal end, and the wall extending between the first open terminal end and the second open terminal end is separate and removable from the container so that the first terminal end and the second terminal end are separated from the container and comprises a shape substantially similar to the container but with smaller dimensions.

21. The system of claim 20, wherein the sleeve defines a funnel shape wherein the first open terminal end is larger than the second open terminal end and the wall extends between the first open terminal end and the second open terminal end.

22. The system of claim 18, wherein at least a portion of the open end of the container is configured to be wrapped about the deformable member, and the deformable member is configured to be crimped to a selected position to maintain the position of at least a portion of the open end of the container.

23. The system of claim 18, wherein the handle is adjacent the closure system.

24. A system for delivering an item to a sterile field by a user, comprising:

a container configured to contain the item within an internal volume defined by an exterior wall, wherein the container includes one opening at a first end of the exterior wall into the internal volume of the container;

a closure system having a deformable member configured to be placed at the first end near the one opening and to close the one opening of the container to an ambient environment;

a handle adjacent to the closure system and extending away from the first end towards a second end of the container, wherein the second end is closed; and a passage system comprising a sleeve having a first open terminal end, a second open terminal end, and a wall extending between the first open terminal end and the second open terminal end, the sleeve provided within the internal volume of the container and configured to be moved partially out of the container at a first time and entirely removed from the container at a second time that is later than the first time;

wherein the item is operable to pass through the sleeve from an exterior environment to the internal volume of the container at the first time;

wherein the container is configured to contain the item in the internal volume after the sleeve is entirely removed at the second time.

25. The system of claim 24, wherein the sleeve defines a funnel shape wherein the first open end is larger than the second open end and the wall extends between the first open terminal end and the second open terminal end and at least the second open terminal end is moveable within the container.

26. The system of claim 24, wherein the closure system is configured to crimp to close the container.

27. The system of claim 24, wherein the closure system is integral with the container and the sleeve is configured to be removed through the closure system and the closure system is configured to close the container after the sleeve is removed.

* * * * *